United States Patent [19]

Göbel et al.

[11] Patent Number: 5,679,558
[45] Date of Patent: Oct. 21, 1997

[54] TRANSFORMATION OF MONOCOT CELLS

[75] Inventors: Elke Göbel, Gent, Belgium; Fumio Nakakido, Shizuoka, Japan

[73] Assignee: Plant Genetic Systems, N.V., Brussels, Belgium

[21] Appl. No.: 318,772

[22] PCT Filed: Apr. 14, 1993

[86] PCT No.: PCT/EP93/00905

§ 371 Date: Mar. 15, 1995

§ 102(e) Date: Mar. 15, 1995

[87] PCT Pub. No.: WO93/21335

PCT Pub. Date: Oct. 28, 1993

[30] Foreign Application Priority Data

Apr. 15, 1992 [EP] European Pat. Off. ............ 92401066

[51] Int. Cl.$^6$ ........................... C12N 15/00; C12N 15/82
[52] U.S. Cl. .................... 435/172.3; 435/172.1; 800/205
[58] Field of Search .................. 800/208; 435/172.3, 435/172.5, 240.4, 204.45, 240.49, 240.5

[56] References Cited

PUBLICATIONS

Lindsey et al., Physiologia Plantarum 79:168–172 Copenhagen 1990.
Lindsey et al., Plant Molecular Biology 10;43–52 (1987).
Proc. Ann. Meeting & 28th Symposium of the Jap. Soc. Plant Physiologist (1988) (Translation attached).
Morikawa et al., Gene, 41:121–124 (1986).
Morikawa et al., Biotechnology in Agriculture, 175–202 (1988).
Lee et al., Korean J. Genetics 11–2:65–72 (1989).
Yang et al. Biological abstracts No. 028273 ACTA BOT SIN vol. 33 No. 11 1991.
Li et al. "Introduction of foreign genes into seed embryo cells of rice by electroinjectioon and the regeneration of transgenic rice plants" Science in china Series B vol. 34 No. 8 1991.
Xu et al. "Gene transfer into intact plant cells by electroporation" ACTA BOT SIN vol.32 No. 10, pp. 759–765, abstract 1991.
Tada et al. "Expression of a monocot LHCP promoter in transgenic rice" vol. 10, No. 7 pp. 1803–1809 1991.

*Primary Examiner*—Gary Benzion
*Attorney, Agent, or Firm*—Birch, Stewart, Kolasch & Birch, LLP

[57] ABSTRACT

A process for genetically transforming the nuclear genome of a cell of a rice plant, comprising the steps of: providing without any enzymatic pretreatment or mechanical cell wall removal a culture of aggregated suspension cells which are preplasmolyzed in a hypertonic buffer, transforming said cells by electroporating and optionally regenerating a transformed plant.

26 Claims, No Drawings

SEQUENCE LISTING ( 1 ) GENERAL INFORMATION:

( i i i ) NUMBER OF SEQUENCES: 2

5,679,558

( 2 ) INFORMATION FOR SEQ ID NO:1:

( i ) SEQUENCE CHARACTERISTICS:
        ( A ) LENGTH: 4883 base pairs
        ( B ) TYPE: nucleic acid
        ( C ) STRANDEDNESS: double stranded
        ( D ) TOPOLOGY: circular ( i i ) MOLECULE TYPE: pDE110 : plasmid DNA replicable in E.coli ( i x ) FEATURE:
        ( D ) OTHER INFORMATION:
            1 - 395 : pUC18 derived sequence
            396 - 1779: "35S3"promoter sequence derived from
            Cauliflower mosaic virus isolate CabbB-JI
            1780 - 2331: coding sequence of phosphinotricin
            acetyltransferase gene
            2332 - 2619: 3'regulatory sequence containing the
            polyadenylation site derived from Agrobacterium
            T-DNA nopaline synthase gene
            2620 - 4883: pUC18 derived sequence
            Other information: plasmid is replicable in E.coli,
            confers ampicillin resistance to the bacterium ( x i ) SEQUENCE DESCRIPTION: SEQ ID NO:1:

```
TCGCGCGTTT  CGGTGATGAC  GGTGAAAACC  TCTGACACAT  GCAGCTCCCG      50
GAGACGGTCA  CAGCTTGTCT  GTAAGCGGAT  GCCGGGAGCA  GACAAGCCCG     100
TCAGGGCGCG  TCAGCGGGTG  TTGGCGGGTG  TCGGGCTGG   CTTAACTATG     150
CGGCATCAGA  GCAGATTGTA  CTGAGAGTGC  ACCATATGCG  GTGTGAAATA     200
CCGCACAGAT  GCGTAAGGAG  AAAATACCGC  ATCAGGCGCC  ATTCGCCATT     250
CAGGCTGCGC  AACTGTTGGG  AAGGGCGATC  GGTGCGGGCC  TCTTCGCTAT     300
TACGCCAGCT  GGCGAAAGGG  GGATGTGCTG  CAAGGCGATT  AAGTTGGGTA     350
ACGCCAGGGT  TTTCCCAGTC  ACGACGTTGT  AAAACGACGG  CCAGTGAATT     400
CCAATCCCAC  CAAAACCTGA  ACCTAGCAGT  TCAGTTGCTC  CTCTCAGAGA     450
CGAATCGGGT  ATTCAACACC  CTCATACCAA  CTACTACGTC  GTGTATAACG     500
GACCTCATGC  CGGTATATAC  GATGACTGGG  GTTGTACAAA  GGCAGCAACA     550
AACGGTGTTC  CCGGAGTTGC  GCATAAGAAG  TTTGCCACTA  TTACAGAGGC     600
AAGAGCAGCA  GCTGACGCGT  ATACAACAAG  TCAGCAAACA  GATAGGTTGA     650
ACTTCATCCC  CAAAGGAGAA  GCTCAACTCA  AGCCCAAGAG  CTTTGCGAAG     700
GCCCTAACAA  GCCCACCAAA  GCAAAAAGCC  CACTGCTCAC  GCTAGGAACC     750
AAAAGGCCCA  GCAGTGATCC  AGCCCCAAAA  GAGATCTCCT  TTGCCCCGGA     800
GATTACAATG  GACGATTTCC  TCTATCTTTA  CGATCTAGGA  AGGAAGTTCG     850
AAGGTGAAGG  TGACGACACT  ATGTTCACCA  CTGATAATGA  GAAGGTTAGC     900
CTCTTCAATT  TCAGAAAGAA  TGCTGACCCA  CAGATGGTTA  GAGAGGCCTA     950
CGCAGCAGGT  CTCATCAAGA  CGATCTACCC  GAGTAACAAT  CTCCAGGAGA    1000
TCAAATACCT  TCCCAAGAAG  GTTAAAGATG  CAGTCAAAAG  ATTCAGGACT    1050
AATTGCATCA  AGAACACAGA  GAAAGACATA  TTTCTCAAGA  TCAGAAGTAC    1100
TATTCCAGTA  TGGACGATTC  AAGGCTTGCT  TCATAAACCA  AGGCAAGTAA    1150
TAGAGATTGG  AGTCTCTAAA  AAGGTAGTTC  CTACTGAATC  TAAGGCCATG    1200
CATGGAGTCT  AAGATTCAAA  TCGAGGATCT  AACAGAACTC  GCCGTGAAGA    1250
CTGGCGAACA  GTTCATACAG  AGTCTTTTAC  GACTCAATGA  CAAGAAGAAA    1300
```

-continued

| | | | | | |
|---|---|---|---|---|---|
| ATCTTCGTCA | ACATGGTGGA | GCACGACACT | CTGGTCTACT | CCAAAAATGT | 1350 |
| CAAAGATACA | GTCTCAGAAG | ACCAAGGGC | TATTGAGACT | TTTCAACAAA | 1400 |
| GGATAATTTC | GGGAAACCTC | CTCGGATTCC | ATTGCCAGC | TATCTGTCAC | 1450 |
| TTCATCGAAA | GGACAGTAGA | AAAGGAAGGT | GGCTCCTACA | AATGCCATCA | 1500 |
| TTGCGATAAA | GGAAAGGCTA | TCATTCAAGA | TGCCTCTGCC | GACAGTGGTC | 1550 |
| CCAAAGATGG | ACCCCACCC | ACGAGGAGCA | TCGTGGAAAA | AGAAGACGTT | 1600 |
| CCAACCACGT | CTTCAAAGCA | AGTGGATTGA | TGTGACATCT | CCACTGACGT | 1650 |
| AAGGGATGAC | GCACAATCCC | ACTATCCTTC | GCAAGACCCT | TCCTCTATAT | 1700 |
| AAGGAAGTTC | ATTTCATTTG | GAGAGGACAC | GCTGAAATCA | CCAGTCTCTC | 1750 |
| TCTATAAATC | TATCTCTCTC | TCTATAACCA | TGGACCCAGA | ACGACGCCCG | 1800 |
| GCCGACATCC | GCCGTGCCAC | CGAGGCGGAC | ATGCCGGCGG | TCTGCACCAT | 1850 |
| CGTCAACCAC | TACATCGAGA | CAAGCACGGT | CAACTTCCGT | ACCGAGCCGC | 1900 |
| AGGAACCGCA | GGAGTGGACG | GACGACCTCG | TCCGTCTGCG | GGAGCGCTAT | 1950 |
| CCCTGGCTCG | TCGCCGAGGT | GGACGGCGAG | GTCGCCGGCA | TCGCCTACGC | 2000 |
| GGGCCCCTGG | AAGGCACGCA | ACGCCTACGA | CTGGACGGCC | GAGTCGACCG | 2050 |
| TGTACGTCTC | CCCCCGCCAC | CAGCGGACGG | GACTGGGCTC | CACGCTCTAC | 2100 |
| ACCCACCTGC | TGAAGTCCCT | GGAGGCACAG | GGCTTCAAGA | GCGTGGTCGC | 2150 |
| TGTCATCGGG | CTGCCCAACG | ACCCGAGCGT | GCGCATGCAC | GAGGCGCTCG | 2200 |
| GATATGCCCC | CCGCGGCATG | CTGCGGGCGG | CCGGCTTCAA | GCACGGGAAC | 2250 |
| TGGCATGACG | TGGGTTTCTG | GCAGCTGGAC | TTCAGCCTGC | CGGTACCGCC | 2300 |
| CCGTCCGGTC | CTGCCCGTCA | CCGAGATCTG | ATCTCACGCG | TCTAGGATCC | 2350 |
| GAAGCAGATC | GTTCAAACAT | TTGGCAATAA | AGTTTCTTAA | GATTGAATCC | 2400 |
| TGTTGCCGGT | CTTGCGATGA | TTATCATATA | ATTTCTGTTG | AATTACGTTA | 2450 |
| AGCATGTAAT | AATTAACATG | TAATGCATGA | CGTTATTTAT | GAGATGGGTT | 2500 |
| TTTATGATTA | GAGTCCCGCA | ATTATACATT | TAATACGCGA | TAGAAAACAA | 2550 |
| AATATAGCGC | GCAAACTAGG | ATAAATTATC | GCGCGCGGTG | TCATCTATGT | 2600 |
| TACTAGATCG | GGAAGATCCT | CTAGAGTCGA | CCTGCAGGCA | TGCAAGCTTG | 2650 |
| GCGTAATCAT | GGTCATAGCT | GTTTCCTGTG | TGAAATTGTT | ATCCGCTCAC | 2700 |
| AATTCCACAC | AACATACGAG | CCGGAAGCAT | AAAGTGTAAA | GCCTGGGGTG | 2750 |
| CCTAATGAGT | GAGCTAACTC | ACATTAATTG | CGTTGCGCTC | ACTGCCCGCT | 2800 |
| TTCCAGTCGG | GAAACCTGTC | GTGCCAGCTG | CATTAATGAA | TCGGCCAACG | 2850 |
| CGCGGGGAGA | GGCGGTTTGC | GTATTGGGCG | CTCTTCCGCT | TCCTCGCTCA | 2900 |
| CTGACTCGCT | GCGCTCGGTC | GTTCGGCTGC | GGCGAGCGGT | ATCAGCTCAC | 2950 |
| TCAAAGGCGG | TAATACGGTT | ATCCACAGAA | TCAGGGGATA | ACGCAGGAAA | 3000 |
| GAACATGTGA | GCAAAAGGCC | AGCAAAAGGC | CAGGAACCGT | AAAAAGGCCG | 3050 |
| CGTTGCTGGC | GTTTTTCCAT | AGGCTCCGCC | CCCCTGACGA | GCATCACAAA | 3100 |
| AATCGACGCT | CAAGTCAGAG | GTGGCGAAAC | CCGACAGGAC | TATAAAGATA | 3150 |
| CCAGGCGTTT | CCCCCTGGAA | GCTCCCTCGT | GCGCTCTCCT | GTTCCGACCC | 3200 |
| TGCCGCTTAC | CGGATACCTG | TCCGCCTTTC | TCCCTTCGGG | AAGCGTGGCG | 3250 |
| CTTTCTCAAT | GCTCACGCTG | TAGGTATCTC | AGTTCGGTGT | AGGTCGTTCG | 3300 |

| | | | | | |
|---|---|---|---|---|---|
| CTCCAAGCTG | GGCTGTGTGC | ACGAACCCCC | CGTTCAGCCC | GACCGCTGCG | 3350 |
| CCTTATCCGG | TAACTATCGT | CTTGAGTCCA | ACCCGGTAAG | ACACGACTTA | 3400 |
| TCGCCACTGG | CAGCAGCCAC | TGGTAACAGG | ATTAGCAGAG | CGAGGTATGT | 3450 |
| AGGCGGTGCT | ACAGAGTTCT | TGAAGTGGTG | GCCTAACTAC | GGCTACACTA | 3500 |
| GAAGGACAGT | ATTTGGTATC | TGCGCTCTGC | TGAAGCCAGT | TACCTTCGGA | 3550 |
| AAAAGAGTTG | GTAGCTCTTG | ATCCGGCAAA | CAAACCACCG | CTGGTAGCGG | 3600 |
| TGGTTTTTTT | GTTTGCAAGC | AGCAGATTAC | GCGCAGAAAA | AAAGGATCTC | 3650 |
| AAGAAGATCC | TTTGATCTTT | TCTACGGGGT | CTGACGCTCA | GTGGAACGAA | 3700 |
| AACTCACGTT | AAGGGATTTT | GGTCATGAGA | TTATCAAAAA | GGATCTTCAC | 3750 |
| CTAGATCCTT | TTAAATTAAA | AATGAAGTTT | TAAATCAATC | TAAAGTATAT | 3800 |
| ATGAGTAAAC | TTGGTCTGAC | AGTTACCAAT | GCTTAATCAG | TGAGGCACCT | 3850 |
| ATCTCAGCGA | TCTGTCTATT | TCGTTCATCC | ATAGTTGCCT | GACTCCCCGT | 3900 |
| CGTGTAGATA | ACTACGATAC | GGGAGGGCTT | ACCATCTGGC | CCCAGTGCTG | 3950 |
| CAATGATACC | GCGAGACCCA | CGCTCACCGG | CTCCAGATTT | ATCAGCAATA | 4000 |
| AACCAGCCAG | CCGGAAGGGC | CGAGCGCAGA | AGTGGTCCTG | CAACTTTATC | 4050 |
| CGCCTCCATC | CAGTCTATTA | ATTGTTGCCG | GGAAGCTAGA | GTAAGTAGTT | 4100 |
| CGCCAGTTAA | TAGTTTGCGC | AACGTTGTTG | CCATTGCTAC | AGGCATCGTG | 4150 |
| GTGTCACGCT | CGTCGTTTGG | TATGGCTTCA | TTCAGCTCCG | GTTCCCAACG | 4200 |
| ATCAAGGCGA | GTTACATGAT | CCCCCATGTT | GTGCAAAAAA | GCGGTTAGCT | 4250 |
| CCTTCGGTCC | TCCGATCGTT | GTCAGAAGTA | AGTTGGCCGC | AGTGTTATCA | 4300 |
| CTCATGGTTA | TGGCAGCACT | GCATAATTCT | CTTACTGTCA | TGCCATCCGT | 4350 |
| AAGATGCTTT | TCTGTGACTG | GTGAGTACTC | AACCAAGTCA | TTCTGAGAAT | 4400 |
| AGTGTATGCG | GCGACCGAGT | TGCTCTTGCC | CGGCGTCAAT | ACGGGATAAT | 4450 |
| ACCGCGCCAC | ATAGCAGAAC | TTTAAAAGTG | CTCATCATTG | GAAAACGTTC | 4500 |
| TTCGGGGCGA | AAACTCTCAA | GGATCTTACC | GCTGTTGAGA | TCCAGTTCGA | 4550 |
| TGTAACCCAC | TCGTGCACCC | AACTGATCTT | CAGCATCTTT | TACTTTCACC | 4600 |
| AGCGTTTCTG | GGTGAGCAAA | AACAGGAAGG | CAAAATGCCG | CAAAAAAGGG | 4650 |
| AATAAGGGCG | ACACGGAAAT | GTTGAATACT | CATACTCTTC | CTTTTTCAAT | 4700 |
| ATTATTGAAG | CATTTATCAG | GGTTATTGTC | TCATGAGCGG | ATACATATTT | 4750 |
| GAATGTATTT | AGAAAAATAA | ACAAATAGGG | GTTCCGCGCA | CATTTCCCCG | 4800 |
| AAAAGTGCCA | CCTGACGTCT | AAGAAACCAT | TATTATCATG | ACATTAACCT | 4850 |
| ATAAAAATAG | GCGTATCACG | AGGCCCTTTC | GTC | | 4883 |

( 2 ) INFORMATION FOR SEQ ID NO:2:

( i ) SEQUENCE CHARACTERISTICS:
        ( A ) LENGTH: 5642 base pairs
        ( B ) TYPE: nucleic acid
        ( C ) STRANDEDNESS: double stranded
        ( D ) TOPOLOGY: circular ( i i ) MOLECULE TYPE: pDE4 : plasmid DNA replicable in E.coli ( i x ) FEATURE:
        ( D ) OTHER INFORMATION:
            1 - 395 : pUC18 derived sequence
            396 - 1284: "35S3" promoter sequence derived from
            Cauliflower mosaic virus isolate CabbB-JI 1285 - 3093: coding sequence of -glucuronidase gene
3094 - 3378: 3'regulatory sequence containing the polyadenylation site derived from Agrobacterium T-DNA nopaline synthase gene
3379 - 5642: pUC18 derived sequence
Other information: plasmid is replicable in E.coli, confers ampicillin resistance to the bacterium ( x i ) SEQUENCE DESCRIPTION: SEQ ID NO:2:

| | | | | | | |
|---|---|---|---|---|---|---|
| TCGCGCGTTT | CGGTGATGAC | GGTGAAAACC | TCTGACACAT | GCAGCTCCCG | | 50 |
| GAGACGGTCA | CAGCTTGTCT | GTAAGCGGAT | GCCGGGAGCA | GACAAGCCCG | | 100 |
| TCAGGGCGCG | TCAGCGGGTG | TTGGCGGGTG | TCGGGGCTGG | CTTAACTATG | | 150 |
| CGGCATCAGA | GCAGATTGTA | CTGAGAGTGC | ACCATATGCG | GTGTGAAATA | | 200 |
| CCGCACAGAT | GCGTAAGGAG | AAAATACCGC | ATCAGGCGCC | ATTCGCCATT | | 250 |
| CAGGCTGCGC | AACTGTTGGG | AAGGGCGATC | GGTGCGGGCC | TCTTCGCTAT | | 300 |
| TACGCCAGCT | GGCGAAAGGG | GGATGTGCTG | CAAGGCGATT | AAGTTGGGTA | | 350 |
| ACGCCAGGGT | TTTCCCAGTC | ACGACGTTGT | AAAACGACGG | CCAGTGAATT | | 400 |
| CGAGCTCGGT | ACCCGGGGAT | CCTCTAGAGT | CGACCTGCAG | GCATGCAAGC | | 450 |
| TCCTACGCAG | CAGGTCTCAT | CAAGACGATC | TACCCGAGTA | ACAATCTCCA | | 500 |
| GGAGATCAAA | TACCTTCCCA | AGAAGGTTAA | AGATGCAGTC | AAAAGATTCA | | 550 |
| GGACTAATTG | CATCAAGAAC | ACAGAGAAAG | ACATATTTCT | CAAGATCAGA | | 600 |
| AGTACTATTC | CAGTATGGAC | GATTCAAGGC | TTGCTTCATA | AACCAAGGCA | | 650 |
| AGTAATAGAG | ATTGGAGTCT | CTAAAAAGGT | AGTTCCTACT | GAATCTAAGG | | 700 |
| CCATGCATGG | AGTCTAAGAT | TCAAATCGAG | GATCTAACAG | AACTCGCCGT | | 750 |
| GAAGACTGGC | GAACAGTTCA | TACAGAGTCT | TTTACGACTC | AATGACAAGA | | 800 |
| AGAAAATCTT | CGTCAACATG | GTGGAGCACG | ACACTCTGGT | CTACTCCAAA | | 850 |
| AATGTCAAAG | ATACAGTCTC | AGAAGACCAA | AGGGCTATTG | AGACTTTTCA | | 900 |
| ACAAAGGATA | ATTTCGGGAA | ACCTCCTCGG | ATTCCATTGC | CCAGCTATCT | | 950 |
| GTCACTTCAT | CGAAAGGACA | GTAGAAAAGG | AAGGTGGCTC | CTACAAATGC | | 1000 |
| CATCATTGCG | ATAAAGGAAA | GGCTATCATT | CAAGATGCCT | CTGCCGACAG | | 1050 |
| TGGTCCCAAA | GATGGACCCC | CACCCACGAG | GAGCATCGTG | GAAAAAGAAG | | 1100 |
| ACGTTCCAAC | CACGTCTTCA | AAGCAAGTGG | ATTGATGTGA | CATCTCCACT | | 1150 |
| GACGTAAGGG | ATGACGCACA | ATCCCACTAT | CCTTCGCAAG | ACCCTTCCTC | | 1200 |
| TATATAAGGA | AGTTCATTTC | ATTTGGAGAG | GACACGCTGA | AATCACCAGT | | 1250 |
| CTCTCTCTAT | AAATCTATCT | CTCTCTCTAT | AACCATGGTC | CGTCCTGTAG | | 1300 |
| AAACCCCAAC | CCGTGAAATC | AAAAAACTCG | ACGGCCTGTG | GCATTCAGT | | 1350 |
| CTGGATCGCG | AAAACTGTGG | AATTGATCAG | CGTTGGTGGG | AAAGCGCGTT | | 1400 |
| ACAAGAAAGC | CGGGCAATTG | CTGTGCCAGG | CAGTTTTAAC | GATCAGTTCG | | 1450 |
| CCGATGCAGA | TATTCGTAAT | TATGCGGGCA | ACGTCTGGTA | TCAGCGCGAA | | 1500 |
| GTCTTTATAC | CGAAAGGTTG | GGCAGGCCAG | CGTATCGTGC | TGCGTTTCGA | | 1550 |
| TGCGGTCACT | CATTACGGCA | AAGTGTGGGT | CAATAATCAG | GAAGTGATGG | | 1600 |
| AGCATCAGGG | CGGCTATACG | CCATTTGAAG | CCGATGTCAC | GCCGTATGTT | | 1650 |
| ATTGCCGGGA | AAAGTGTACG | TATCACCGTT | TGTGTGAACA | ACGAACTGAA | | 1700 |
| CTGGCAGACT | ATCCCGCCGG | GAATGGTGAT | TACCGACGAA | AACGGCAAGA | | 1750 |

```
AAAAGCAGTC TTACTTCCAT GATTTCTTTA ACTATGCCGG AATCCATCGC       1800
AGCGTAATGC TCTACACCAC GCCGAACACC TGGGTGGACG ATATCACCGT       1850
GGTGACGCAT GTCGCGCAAG ACTGTAACCA CGCGTCTGTT GACTGGCAGG       1900
TGGTGGCCAA TGGTGATGTC AGCGTTGAAC TGCGTGATGC GGATCAACAG       1950
GTGGTTGCAA CTGGACAAGG CACTAGCGGG ACTTTGCAAG TGGTGAATCC       2000
GCACCTCTGG CAACCGGGTG AAGGTTATCT CTATGAACTG TGCGTCACAG       2050
CCAAAAGCCA GACAGAGTGT GATATCTACC CGCTTCGCGT CGGCATCCGG       2100
TCAGTGGCAG TGAAGGGCGA ACAGTTCCTG ATTAACCACA AACCGTTCTA       2150
CTTTACTGGC TTTGGTCGTC ATGAAGATGC GGACTTACGT GGCAAAGGAT       2200
TCGATAACGT GCTGATGGTG CACGACCACG CATTAATGGA CTGGATTGGG       2250
GCCAACTCCT ACCGTACCTC GCATTACCCT TACGCTGAAG AGATGCTCGA       2300
CTGGGCAGAT GAACATGGCA TCGTGGTGAT TGATGAAACT GCTGCTGTCG       2350
GCTTTAACCT CTCTTTAGGC ATTGGTTTCG AAGCGGGCAA CAAGCCGAAA       2400
GAACTGTACA GCGAAGAGGC AGTCAACGGG GAAACTCAGC AAGCGCACTT       2450
ACAGGCGATT AAAGAGCTGA TAGCGCGTGA CAAAAACCAC CCAAGCGTGG       2500
TGATGTGGAG TATTGCCAAC GAACCGGATA CCCGTCCGCA AGTGCACGGG       2550
AATATTTCGC CACTGGCGGA AGCAACGCGT AAACTCGACC CGACGCGTCC       2600
GATCACCTGC GTCAATGTAA TGTTCTGCGA CGCTCACACC GATACCATCA       2650
GCGATCTCTT TGATGTGCTG TGCCTGAACC GTTATTACGG ATGGTATGTC       2700
CAAAGCGGCG ATTTGGAAAC GGCAGAGAAG GTACTGGAAA AAGAACTTCT       2750
GGCCTGGCAG GAGAAACTGC ATCAGCCGAT TATCATCACC GAATACGGCG       2800
TGGATACGTT AGCCGGGCTG CACTCAATGT ACACCGACAT GTGGAGTGAA       2850
GAGTATCAGT GTGCATGGCT GGATATGTAT CACCGCGTCT TTGATCGCGT       2900
CAGCGCCGTC GTCGGTGAAC AGGTATGGAA TTTCGCCGAT TTTGCGACCT       2950
CGCAAGGCAT ATTGCGCGTT GGCGGTAACA AGAAAGGGAT CTTCACTCGC       3000
GACCGCAAAC CGAAGTCGGC GGCTTTTCTG CTGCAAAAAC GCTGGACTGG       3050
CATGAACTTC GGTGAAAAAC CGCAGCAGGG AGGCAAACAA TGAXXXXXXG       3100
AATTGATCCG AAGCAGATCG TTCAAACATT TGGCAATAAA GTTTCTTAAG       3150
ATTGAATCCT GTTGCCGGTC TTGCGATGAT TATCATATAA TTTCTGTTGA       3200
ATTACGTTAA GCATGTAATA ATTAACATGT AATGCATGAC GTTATTTATG       3250
AGATGGGTTT TTATGATTAG AGTCCCGCAA TTATACATTT AATACGCGAT       3300
AGAAAACAAA ATATAGCGCG CAAACTAGGA TAAATTATCG CGCGCGGTGT       3350
CATCTATGTT ACTAGATCGG GAAGATCCTC TAGAGTCGAC CTGCAGGCAT       3400
GCAAGCTTGG CGTAATCATG GTCATAGCTG TTTCCTGTGT GAAATTGTTA       3450
TCCGCTCACA ATTCCACACA ACATACGAGC CGGAAGCATA AAGTGTAAAG       3500
CCTGGGGTGC CTAATGAGTG AGCTAACTCA CATTAATTGC GTTGCGCTCA       3550
CTGCCCGCTT TCCAGTCGGG AAACCTGTCG TGCCAGCTGC ATTAATGAAT       3600
CGGCCAACGC GCGGGGAGAG GCGGTTTGCG TATTGGGCGC TCTTCCGCTT       3650
CCTCGCTCAC TGACTCGCTG CGCTCGGTCG TTCGGCTGCG GCGAGCGGTA       3700
TCAGCTCACT CAAAGGCGGT AATACGGTTA TCCACAGAAT CAGGGGATAA       3750
```

| | | | | | |
|---|---|---|---|---|---|
| CGCAGGAAAG | AACATGTGAG | CAAAAGGCCA | GCAAAAGGCC | AGGAACCGTA | 3800 |
| AAAAGGCCGC | GTTGCTGGCG | TTTTTCCATA | GGCTCCGCCC | CCCTGACGAG | 3850 |
| CATCACAAAA | ATCGACGCTC | AAGTCAGAGG | TGGCGAAACC | CGACAGGACT | 3900 |
| ATAAAGATAC | CAGGCGTTTC | CCCCTGGAAG | CTCCCTCGTG | CGCTCTCCTG | 3950 |
| TTCCGACCCT | GCCGCTTACC | GGATACCTGT | CCGCCTTTCT | CCCTTCGGGA | 4000 |
| AGCGTGGCGC | TTTCTCAATG | CTCACGCTGT | AGGTATCTCA | GTTCGGTGTA | 4050 |
| GGTCGTTCGC | TCCAAGCTGG | GCTGTGTGCA | CGAACCCCC | GTTCAGCCCG | 4100 |
| ACCGCTGCGC | CTTATCCGGT | AACTATCGTC | TTGAGTCCAA | CCCGGTAAGA | 4150 |
| CACGACTTAT | CGCCACTGGC | AGCAGCCACT | GGTAACAGGA | TTAGCAGAGC | 4200 |
| GAGGTATGTA | GGCGGTGCTA | CAGAGTTCTT | GAAGTGGTGG | CCTAACTACG | 4250 |
| GCTACACTAG | AAGGACAGTA | TTTGGTATCT | GCGCTCTGCT | GAAGCCAGTT | 4300 |
| ACCTTCGGAA | AAAGAGTTGG | TAGCTCTTGA | TCCGGCAAAC | AAACCACCGC | 4350 |
| TGGTAGCGGT | GGTTTTTTTG | TTTGCAAGCA | GCAGATTACG | CGCAGAAAAA | 4400 |
| AAGGATCTCA | AGAAGATCCT | TTGATCTTTT | CTACGGGGTC | TGACGCTCAG | 4450 |
| TGGAACGAAA | ACTCACGTTA | AGGGATTTTG | GTCATGAGAT | TATCAAAAAG | 4500 |
| GATCTTCACC | TAGATCCTTT | TAAATTAAAA | ATGAAGTTTT | AAATCAATCT | 4550 |
| AAAGTATATA | TGAGTAAACT | TGGTCTGACA | GTTACCAATG | CTTAATCAGT | 4600 |
| GAGGCACCTA | TCTCAGCGAT | CTGTCTATTT | CGTTCATCCA | TAGTTGCCTG | 4650 |
| ACTCCCCGTC | GTGTAGATAA | CTACGATACG | GGAGGGCTTA | CCATCTGGCC | 4700 |
| CCAGTGCTGC | AATGATACCG | CGAGACCCAC | GCTCACCGGC | TCCAGATTTA | 4750 |
| TCAGCAATAA | ACCAGCCAGC | CGGAAGGGCC | GAGCGCAGAA | GTGGTCCTGC | 4800 |
| AACTTTATCC | GCCTCCATCC | AGTCTATTAA | TTGTTGCCGG | GAAGCTAGAG | 4850 |
| TAAGTAGTTC | GCCAGTTAAT | AGTTTGCGCA | ACGTTGTTGC | CATTGCTACA | 4900 |
| GGCATCGTGG | TGTCACGCTC | GTCGTTTGGT | ATGGCTTCAT | TCAGCTCCGG | 4950 |
| TTCCCAACGA | TCAAGGCGAG | TTACATGATC | CCCCATGTTG | TGCAAAAAAG | 5000 |
| CGGTTAGCTC | CTTCGGTCCT | CCGATCGTTG | TCAGAAGTAA | GTTGGCCGCA | 5050 |
| GTGTTATCAC | TCATGGTTAT | GGCAGCACTG | CATAATTCTC | TTACTGTCAT | 5100 |
| GCCATCCGTA | AGATGCTTTT | CTGTGACTGG | TGAGTACTCA | ACCAAGTCAT | 5150 |
| TCTGAGAATA | GTGTATGCGG | CGACCGAGTT | GCTCTTGCCC | GGCGTCAATA | 5200 |
| CGGGATAATA | CCGCGCCACA | TAGCAGAACT | TTAAAAGTGC | TCATCATTGG | 5250 |
| AAAACGTTCT | TCGGGGCGAA | AACTCTCAAG | GATCTTACCG | CTGTTGAGAT | 5300 |
| CCAGTTCGAT | GTAACCCACT | CGTGCACCCA | ACTGATCTTC | AGCATCTTTT | 5350 |
| ACTTTCACCA | GCGTTTCTGG | GTGAGCAAAA | ACAGGAAGGC | AAAATGCCGC | 5400 |
| AAAAAAGGGA | ATAAGGGCGA | CACGGAAATG | TTGAATACTC | ATACTCTTCC | 5450 |
| TTTTTCAATA | TTATTGAAGC | ATTTATCAGG | GTTATTGTCT | CATGAGCGGA | 5500 |
| TACATATTTG | AATGTATTTA | GAAAAATAAA | CAAATAGGGG | TTCCGCGCAC | 5550 |
| ATTTCCCCGA | AAAGTGCCAC | CTGACGTCTA | AGAAACCATT | ATTATCATGA | 5600 |
| CATTAACCTA | TAAAAATAGG | CGTATCACGA | GGCCCTTTCG | TC | 5642 |

TRANSFORMATION OF MONOCOT CELLS

This invention relates to a rapid and efficient method for transforming walled cells of monocotyledonous plants, especially gramineous plants, particularly rice, wheat, corn, barley and other major cereals.

This invention also relates to novel transgenic monocotyledonous plants, particularly gramineous plants, obtainable by this method.

BACKGROUND OF THE INVENTION

In recent years, there has been a tremendous expansion of the capabilities for the genetic engineering of plants. Transgenic plants of many dicotyledonous plant species have been produced. However, many species of plants, especially those belonging to the Monocotyledonae and particularly the Gramineae including economically important species such as corn, wheat and rice, have proven to be very recalcitrant to stable genetic transformation.

Difficulties that have been encountered have resided principally in the inability to combine integrative transformation of monocot plant cells (i.e., the stable insertion of foreign DNA in the nuclear genome of the plant cells) with the regeneration of fertile adult plants from those transformed cells. It has been suggested that such difficulties have been predominantly due to the nonavailability of cells that are competent with respect to 1) DNA uptake, 2) integration of DNA in the genome, and 3) regeneration capability (Potrykus I. (1990) Bio/Technology 9:535). Various methods used to transform cereals have been reviewed in the light of the criteria necessary to assess the stable transformation (Potrykus I. (1990) Bio/Technology 9:535; Potrykus (1991) Annu.Rev.Plant Physiol. Plant Mol. Biol. 42:205). In general, direct gene transfer into protoplasts (by polyethyleneglycol (PEG) treatment and/or electroporation) seams to have had the best potential but has nevertheless been hampered by the fact that regeneration from protoplasts has boon difficult to achieve for most genotypes. In practice, protoplasts have most often been obtained from cell suspension cultures (Lazzeri and Lörz (1988) Advances in Cell Culture Vol. 6, Academic press, p. 291 Ozias-Akins and Lörz (1994) Trends in Biotechnology 2:119, Hodges et al (1991) In "Rice Biotechnology" ed. Khush end Toenniessen, C.A.B. International, United Kingdom, p. 157; Lynch et al, (1991) In "Rice Biotechnology" ed. Khush and Toenniessen, C.A.B. International, United Kingdom, p. 135).

As plant regeneration from protoplasts has generally been limited to a relatively small number of genotypes for various species, it has been difficult to develop a generally-effective protoplast-based procedure. Therefore, other approaches have recently been explored, particularly in rice.

Lee et al (1991) Proc. Natl. Acad. Sci. USA ("PNAS") 88:6389 have reported the PEG-mediated transformation of small rice cell groups, obtained from rice suspension cultures. Plantlets that had been stably transformed with the gone encoding β-glucuronidase (gus) and a gone encoding neomycin phosphotransferase II (neo) could be regenerated.

Christou et al (1991) Biotechnology 9:957 have reported the transformation of cells of immature zygotic embryos by bombarding the embryos with DNA-coated gold particles. Transgenic rice plants containing the gus gone with either a gene conferring resistance to phosphinothricin (bar) or to hygromycin (hyg) could be regenerated. The introduced genes were reported to segregate in a normal Mendelian ratio in the progeny.

Introduction of DNA into intact plant cells by means of electroporation—a process that is often referred to as electroinjection (see review by Moriwaka et al (1988).

SUMMARY OF THE INVENTION

The present invention provides a method for genetically transforming the genome, particularly the nuclear genome, of cells of a monocotyledonous plant. The genome is stably transformed. The method is preferably applied to an aggregate of the cells and can be applied to cells which can be cultured in suspension. The cells to be transformed are cells which retain at least a portion of their cell wall. The cells of any plant from which regenerable suspension cultures can be made can be transformed.

The process of the present method comprises electroporating the cells to be transformed in the presence of a DNA fragment.

The DNA used in the transformation is preferably linearized and contains a selectable marker gene, which can be an antibiotic or herbicide resistance gene.

When walled cells from a regenerable suspension culture are used in the present method, the transformed cells can form a callus (i.e. a morphogenic or regenerable callus), from which phenotypically normal (e.g., fertile) pints can be regenerated either by means of organogenesis or, preferably, embryogenesis. Thereby, the resulting transformed cells of this invention can be grown into callus, and plants, preferably phenotypically normal plants, which stably possess and express the one or more genes of interest located on the one or more DNA fragments, can then be regenerated. Such regenerated plants (particularly barley, rice and wheat), as well as their offspring, their seeds, and their transformed cells also form part of this invention.

DETAILED DESCRIPTION OF THE INVENTION

In carrying out the method of this invention, cultures of suspended plant cells having at least part of their plant cell walls, such as cell suspension cultures, can be obtained from monocotyledonous plants in a conventional manner (Li et al (1990) Plant Mol. Biol. Rep. 8:276 Wen et al (1991) Plant Mol. Biol. Rep. 9:308 Hodges et al (1991) In "Rice Biotechnology" ed. Khush and Toenniessen, C.A.B. International, United Kingdom, p. 157; Yang et al (1991) Aust.J.Plant Physiol. 18:445; Redway et al (1990) Plant Cell Reports 8:714; Jähne et al (1991) Theor.Appl.Genet. 82:74; Gordon-Kamm et al (1990) The Plant Cell 2:603; Fromm et al (1990) Bio/Technology 8:833; Rhodes et al (1988) Bio/Technology 6:56; Vasil and Vasil (1986) J.Plant Physiol. 124:399; Kamo and Hodges (1986) Plant Science 45:111). Since cell suspension cultures have typically been generated so as to provide protoplasts, which can then be transformed and cultured to produce transgenic plants, procedures for making such cell cultures have generally been directed towards establishing and maintaining regenerable suspension cultures (i.e., cell suspension cultures from which regenerable callus can be obtained). However, since regeneration in cereals occurs mainly means of embryogenesis, cell suspension cultures of cereals, from which regenerable (in this case, callus can be obtained, will generally be embryogenic suspension cultures. Hence, in the following Description and Examples, the method of this invention is described mainly with reference to embryogenic suspension cultures cereals, such as rice, as a starting material. However, the method of the invention can be applied to any culture suspended walled cells obtained from any monocotyledonous plant species, particularly to any culture of regenerable suspended cells, including any culture of cells regenerable by organogenesis, as well as to walled monocotyledonous cells which can be used to form such cultures of suspended walled cells. Preferred cultures of suspended cells are the various types of liquid cultures which can be obtained by conventional methods, in the course of establishing cell suspension cultures, and which are characterized by: initially, suspended callus clumps, and later, progressively more homogeneous suspended cell aggregates in liquid culture media. The method of this invention is equally applicable to the initial and the later stages but will be particularly exemplified with respect to preferred cultures of suspended cell clumps or aggregates.

Whether a culture of suspended walled cells, such as a culture of suspended cell clumps or a cell suspension culture (e.g., an embryogenic suspension culture), of a particular line of a monocot species (e.g., rice) is suitable for plant regeneration can be determined by plating a large number (i.e., at least 100) of cell aggregates derived from the suspension (or calli derived from such cell aggregates on a suitable propagation medium) on a suitable regeneration medium and determining what proportion of the aggregates give rise to phenotypically normal, fertile plants. If normal fertile plants are obtained from at least about 10%, preferably at least 25%, particularly at least 50%, of the cell aggregates, the suspension culture can be considered to be suitable for the purposes of using the method of this invention to obtain transgenic monocotyledonous plants.

Embryogenic suspension cultures of this invention can be established and maintained by conventional procedures. The embryogenic suspension cultures can generally be described as fast growing and homogeneous in cell type. They consist of well-dispersed aggregates, which are composed of a few to approximately 200 tightly packed embryogenic cells, in livid (e.g., aqueous) medium. The embryogenic cells are round- or oval-shaped, actively dividing and rich in cytoplasm, they can contain lipid droplets and starch grains, and they retain at least part, preferably all, of their cell walls. The embryogenic cells can have doubling times of, for example, 27 to 32 hours and, after plating on suitable media, can give rise to embryogenic calli, from which plants can be regenerated. The specific appearance and characteristics of a given regenerable suspension culture, for example the size of cell clusters, the growth rate, or the color, and the time required for establishing the suspension culture, may depend on the plant species and cultivar use, on the media, and on the physical culture conditions. Cultures of suspended cells that are not cell suspension cultures (i.e., cultures of suspended cell clumps) will generally consist essentially of cell aggregates that 1) are relatively more heterogeneous in size (and the cultures may even contain a large number of relatively large cell clumps) and cell type, and 2) contain cells that readily divide and generally do not show signs of necrosis (e.g., browning). Procedures that can be used for establishing and maintaining embryogenic suspension cultures have been described, for example, for: rice (Li et al (1990) Plant Mol. Biol. Rep. 8:276; Wen et al (1991) Plant Mol. Biol. Rep. 9:308; Hodges et al (1991) In "Rice Biotechnology" ed. Khush and Toenniessen, C.A.B. International, United Kingdom, p. 157), wheat (Yang et al (1991) Aust.J.Plant Physiol. 18:445; Redway et al (1990) Plant Cell Reports 8:714), barley (Jähne et al (1991) Theor.Appl.Genet. 82:74), and corn (Gordon-Kamm et al (1990) The Plant Cell 2:603; Fromm et al (1990) Bio/Technology 8:833; Rhodes et al (1988) Bio/Technology 6:56;Vasil and Vasil (1986) J.Plant Physiol. 124:399; Kamo and Hodges (1986) Plant Science 45:111).

Likewise, general procedures for establishing cultures, especially regenerable cultures, of suspended cells, particularly of cell clumps, of this invention are well known to those skilled in the art. In fact, media and procedures that are conventionally used during the establishment of cell suspension cultures can generally be used for the establishment of such cultures of suspended cells, irrespective of whether cell suspension cultures could be obtained from them. In fact, it is believed that the establishment of such a culture of suspended cells is generally easier than the establishment of a cell suspension culture.

Explants that can be used to induce callus, from which suitable cultures of suspended cells of this invention can be obtained, are well known. For rice, for example, such explants include dry seeds, immature embryos, young leaf bases, immature inflorescenses, anthers, microspores, nodes and roots (particularly root tips), but for other cereals, some of the above explants cannot be used as effectively. It is generally believed that immature embryos are the preferred explants for the induction of callus, particularly regenerable callus. It is believed, however, that those skilled in the art will generally be able to modify and optimize existent media and procedures for use with particular plant species or for particular lines and genotypes within a plant species.

For the purposes of this invention, particularly where the transformed cells are to be regenerated into transgenic plants, it is preferred that the suspension cultures be relatively young, preferably not older than about four months, especially not older than three months, particularly for suspensions of rice cells. Thus, it is often preferred that electroporation of suspended cells, as described below, be carried out before the fourth month, preferably before the third month, after initiation of the suspension culture. It is also preferred that the majority of the cells of the embryogenic suspension culture have a chromosome number that is normal for the plant species, from which the culture is derived. In this respect, it is preferred that at least about 50%, preferably at least 75%, particularly 80%, quite particularly 90%, of such cells have a normal chromosome number. Hence, cultures of suspended cells are preferably used which are significantly younger than established cell suspension cultures in order to reduce significantly any somaclonal variations and other adverse effects in plants that are regenerated from such cells.

The present invention is based on the surprising finding that cultures of suspended walled monocotyledonous cells, particularly cultures of such cells from which regenerable (e.g., embryogenic) callus can be obtained, especially relatively young embryogenic suspension cultures of such cells, as well as walled monocotyledonous cells capable of being used to form such cultures of suspended cells, are competent, not only with respect to regeneration of phenotypically normal plants, but also with respect to DNA uptake by means of electroporation and to subsequent integrative transformation.

The walled monocot cells, to be transformed by the method of this invention, will usually be part of cell aggregates. Whenever such cell aggregates are obtained from cell suspension cultures, particularly embryogenic cell suspension cultures, such cell aggregates will consist of a few to several hundred (i.e., up to about 500) cells and will generally have an average diameter that is smaller than about 0.5 mm. When such cell aggregates are obtained from tissue or callus, preferably regenerable callus, that can be used to form a liquid culture of cell aggregates, they will usually be much larger, with an average diameter of between about 0.5 and 3 mm, preferably with an average diameter of between 1 and 2 mm. When such cell aggregates are obtained from a liquid culture of suspended cells such as from a culture obtained during the establishment of a cell supension culture, they will generally be rather heterogeneous in size, with average dimensions between about 0.5 and 3 mm. However, the dimensions of cell aggregates, described above and in the Examples, are considered preferred dimensions in view of the dimensions of the electroporation cuvettes, which are described below, and are not necessary dimensions for this invention.

In accordance with this invention, electroporation can be carried out in a conventional manner (see, e.g., Fromm et al (1987) Meth. Enzymol. 153:351). In this regard, walled cells, particularly aggregates of walled cells much as are contained in a culture of suspended cells (e.g., an embryogenic suspension culture) or such as can be used to form such a culture, can be transferred to a cuvette suitable for use with an electroporation apparatus (e.g., as described by Dekeyser et al (1990) The Plant Cell 2:591). Alternatively, the walled cells, particularly aggregates thereof, can be suspended in electroporation buffer and transferred by pipette to the cuvette, or the liquid medium can be removed from a suspension culture and its walled cells can then be transferred by spatula to cuvettes that already contain a suitable volume of electroporation buffer. Preferably, about 30 mg to 150 mg, particularly 50 mg to 125 mg, most particularly 75 mg to 100 mg, of cell aggregates per 100 to 200 µl, preferably 100 to 150 µl, of electroporation buffer are transferred to the cuvette.

Prior to transfer to the cuvettes, it is preferred that the walled cell aggregates be suspended in the electroporation buffer, preferably while shaking, for a period of about 15 minutes to 3 hours, preferably for a period of about 45 minutes to 1.5 hours, but the period can be decreased down to a few (i.e., 1 to 5) minutes. Also, the incubation of a cell material need not be carried out in the electroporation buffer but can in fact be carried out in any hypertonic buffer.

Prior to electroporation, it may also be desirable to treat briefly the cell aggregates with plant cell wall-degrading enzymes or with mechanical forces (such as sieving through a fine mesh) in order to damage slightly the cell walls or to make the cell aggregates more homogenous in size. When used, such an enzyme pretreatment should preferably not be for longer than 30 minutes, particularly not for longer than 10 minutes, quite particularly not for longer than 3 to 5 minutes. Enzymes or enzyme compositions that can be used for this purpose are well known (see, e.g., Power and Chapman (1985) In "Plant Cell tissue Culture: A Practical Approach", IRL Press, Oxford).

After the DNA fragments are added to the cuvette containing the walled cells, particularly aggregates thereof, in electroporation buffer, the electroporation can be carried out in accordance with this invention. Preferably, the DNA is coincubated for as long as about two or three hours or as little as about five to fifteen minutes (and as low as about one minute), but typically for about one hour, with the walled cells prior to electroporation. It is believed that best results can be obtained with linear, rather than circular, DNA of relatively small size, preferably smaller than about 20 kb, especially smaller than 15 kb, particularly smaller than 10 kb, quite particularly smaller than 6 kb (e.g., down to about 2–3 kb). In this regard, multiple linear DNA fragments of different composition can be used to transform the competent monocot plant cells of this invention with multiple genes of interests. Preferably, about 5 to 30 µg, particularly about 10 to 25 µg, quite particularly about 10 or 20 µg, of DNA are added to the cuvette containing the cell aggregates. Substances that prevent DNA degradation, such as spermidine, can be added.

Particular electroporation conditions are not believed to be critical, and good results can be obtained (e.g., in rice) with one pulse with an electrical field strength of between about 600 and 700 V/cm discharged from a capacitor of about 800 to 900 µF. Although optimal electroporation conditions for different types of cells and their aggregates (e.g., from suspension cultures) are likely to be different, conditions as described by Fromm et al (1987) Meth. Enzymol. 153:351 and Dekeyser et al (1990) supra can generally be used. In this regard, optimal electroporation conditions for any type of cell aggreate are believed to be dependent on the plant species, being transformed and, when using suspension cultures, the age and general condition of the suspension, and such conditions can be experimentally determined. Hence, it is generally preferred that an exploratory experiment to be carried out initially with the cell aggregates, in which experiment no DNA is added to the electroporation cuvette containing the cell aggregates in electroporation buffer and that, after the electroporation pulse, at least about 50%, preferably at least 75%, particularly at least 90%, of the cell aggregates develop into calli after plating on solid culture medium.

The composition of the electroporation buffer is also not believed to be critical, and generally, conventional electroporation buffers can be used (see, e.g., Fromm et al (1987) supra).

When the transformation by electroporation is completed, the cell aggregates, containing the transformed monocot cells, are transferred to a suitable culture medium (which may be a solid medium, a bead-type medium, or even a liquid medium), preferably a selective medium when the transformed cells contain DNA fragments encoding a selectable marker. This transfer should be as soon as possible after, preferably immediately after, the transformation event and especially within about one to three days after the transformation event.

Preferably, cell aggregates transformed with DNA fragments encoding a selectable marker are cultured using conventional culture conditions, culture procedures, and culture media (see, e.g., references in Vasil (1988) supra) supplemented with a selective agent. The selection of the selective agent will depend on the selectable marker used in the DNA fragments to transform the walled cells, as discussed below. The concentration of the selective agent should provide a suitable selective pressure on the transformed cells so that only stably transformed cells, in which the DNA fragments encoding the selectable marker are integrated, preferably fully integrated, in the genome of the cells, survive and can be isolated. Although such transformed cell aggregates can be cultured for a few days on non-selective medium, it is preferred that they be transferred to selective medium as soon as possible and maintained for a sufficiently long period (e.g., as long as about six months), preferably at least about one month, especially two to three months, to produce significant amounts of transformed morphogenic callus, such as transformed embryogenic callus, which can be used to regenerate a phenotypically normal plant. It is also preferred that the hypertonicity of the medium be maintained for a limited time (e.g., up to about two to three weeks), for instance by supplementing the medium with mannitol.

In accordance with this invention, any DNA fragment can be integrated in the genome, particularly the nuclear genome, of a monocotyledonous plant. Generally, the DNA fragment contains a foreign or endogenous gene or other DNA sequence which is functional in the transformed plant cells and confers an additional property to such cells and to plants regenerated from the cells. To this end, the DNA fragment preferably comprises one or more chimaeric genes which contain the following operably linked DNA sequences: 1) a promoter sequence capable of directing expression of a coding sequence in the plant cell (a "promoter"); 2) a sequence (a "coding sequence") coding for a protein with a specific activity within the plant cell (a "protein of interest"): and 3) suitable 3' transcription regulation signals. In order to obtain the required functionality of the protein, it may also be necessary that the protein be targeted to one or more particular compartments of the plant cell, such as the cytosol, mitochondria, chloroplasts or endoplasmatic reticulum. For targeting to the cytosol, the chimaeric gene(s), as described above, can be used as such. However for targeting to the other compartments, it is required that there be an additional sequence (a "targeting sequence") between the DNA sequences 1) and 2) of the chimaeric gene(s). If required, the chimaeric gene(s) can also contain transcriptional and/or translational enhancers, and the codon usage of the DNA sequences can be optimized or expression in plant cells.

Chimaeric genes in accordance with this invention can be constructed according to well-established principles and techniques. In this regard, the various DNA sequences should be linked so that translation is initiated at the initiation codon of the coding sequence of the protein (or of the targeting sequence, when present).

It is believed that the various constitutive and organ- and tissue-specific promoters that are presently used to direct expression of genes in transformed dicotyledonous plants will also be suitable for use in transformed monocots of this invention. In this regard, particular plant cells can be transformed with a chimaeric gene comprising: a coding sequence encoding a protein of interest and upstream (i.e., 5') thereof, either a foreign or an endogenous promoter suitable for expression of the coding sequence. Suitable foreign constitutive promoters include: the promoter of the cauliflower mosaic virus ("CaMV") isolates CM1841 (Gardner et al (1981) Nucl. Acids. Res. 9:2871) and CabbB-B (Franck et al (1980) Cell, 21:285) (the "35S promoter") which directs constitutive expression of heterologous genes (Odell et al (1983) Nature 313:810); a related promoter (the "3583 promoter") which can be isolated from the CaMV isolate CabbB-JI (Hull and Howell (1978) Virology 86:482) and which differs from the 35S promoter in its sequence (the sequence of the 3583 promoter is disclosed in European patent publication ("EP") 359617) and in its greater activity in transgenic plants (Harpster et al (1988) Mol. Gen. Genet. 212:182) and the TR1' and the TR2' promoters which drive the expression of the 1' and 2' genes, respectively, of the T-DNA of Agrobacterium (Velten et al (1984) EMBO J. 3:2723) and are wound-induced promoters. Suitable organ-specific, tissue-specific and/or inducible foreign promoters are also known (see, e.g., references cited in Kuhlemeier et al (1987) Ann. Rev. Plant Physiol. 38:221) such as the promoters of the small subunit genes (such as the 1A gene) of 1,5-ribulose bisphosphate carboxylase of *Arabidopsis thaliana* (the "ssu" promoter) which are light inducible promoters (Krebbers et al (1988) Plant Mol. Biol. 11:745) active only in photosynthetic tissue; the anther-specific promoters disclosed in EP 344029: and the seed-specific promoters of, for example, *Arabidopsis thaliana* (Krebbers et al (1988) Plant Physiol. 87:859). Promoters of particular usefulness for transforming monocots to render them male-sterile, as described in European patent publication ("EP") 344029, are the tapetum-specific promoters PTA29, PTA26 and PTA13, particularly PTA29, of EP 344029.

Likewise, it is believed that known 3' transcription regulation sequences and polyadenylation signals used in transformed dicotyledonous plants can be used in transformed monsters of this invention. Such 340 transcription regulation signals can be provided downstream (i.e. 3') of the coding sequence. In this regard, a particular plant cell can be transformed with a chimaeric gone containing either foreign or endogenous, transcription termination and polyadenylation signals suitable for obtaining expression of the chimaeric gene. For example, the foreign 3' untranslated ends of genes, such as gene 7 (Veltan and Schell (1985) Nucl. Acids Res. 13:6998), the octopine synthase gene (Gielen et al (1983) EMBO J. 3:835) and the nopaline synthase gene of the T-DNA region of *Agrobacterium tumefaciens* Ti-plasmid can be used.

For construction of a chimaeric gene which can be expressed in a transformed plant cell, preferably in its cytoplasm followed by translocation of its protein of interest to the cell's mitochondria, chloroplasts and/or lumen of the endoplasmatic reticulum, suitable targeting sequences are known. Selection of such targeting sequences is not believed to be critical, and a particular plant cell can be transformed with a chimaeric gene containing either a foreign or endogenous targeting sequence encoding a targeting peptide which will provide translocation of the expression product of the gene. By "targeting peptide" is meant a polypeptide fragment which is normally associated, in an eucaryotic cell, with a chloroplast or mitochondrial protein or subunit of the protein or with a protein translocated to the endoplasmatic reticulum and which is produced in a cell as part of precursor protein encoded by the nuclear DNA of the cell. The targeting peptide is responsible for the translocation process of the nuclear-encoded chloroplast or mitochondrial protein or subunit into the chloroplast or the mitochondria or the lumen the endoplasmatic reticulum. During the translocation process, the targeting peptide is separated or proteolytically removed from the protein or subunit. A targeting sequence can be provided in the chimaeric gene to express a targeting peptide which can translocate an expressed protein of interest within a transformed plant cell as generally described in European patent applications ("EPA") 85402596.2 and 88402222.9. A suitable targeting peptide for transport into chloroplasts is the transit peptide of the small subunit of the enzyme 1,5-ribulose bisphosphate carboxylase (Krebbers et al (1988) Plant Mol. Biol. 11:745 EPA 85402596.2), but other chloroplast transit peptides, such as those listed by Watson (1924) Nucl. Acids Res. 12:5145 and Von Heijne et al (1991) Plant Mol. Biol. Rep. 9:104, can also be used. Suitable mitochondrial targeting peptides are the mitochondrial transit peptides as described by Schatz (1987) Eur. J. Biochem. 165:1 and listed by Watson (1924) supra. Suitable targeting peptides that can translocate a protein of interest to the lumen of the endoplasmatic reticulum of a plant cell are, for instance, the signal peptides described by Von Heijne (1988) Biochem. Biophys. Acta 947:307 and listed by Watson (1984) supra.

Coding sequences that can be used in the production transgenic dicotyledonous plants arm well known (see, for example, the coding sequences listed in Weising et al (1982) Annual Rev. Genet. 22:421), and it is believed that such coding sequences can be put to equally good use in transformed monocotyledonous plants in accordance with this invention. In this respect, the coding sequences can be either foreign or endogenous to the plants and can, for example, code for proteins which: are toxic to insect species, thus protecting the plants against insect attack (EP 193259, EP 305275 and EP 358557); protect the plants against stress conditions (EP 359617) confer on the plants a resistance or tolerance to specific herbicides (EP 242236); kill or disable plant cells in which the proteins are expressed so that, when the coding sequences are under the control of a male or female organ-specific promoter (EP 344029, WO 92/00274 and WO 92/00275), the proteins can render the plants respectively male sterile (EP 344029) or female sterile (EP 412006); can be extracted from the plants or selected plant organs and optionally be further processed so that the plants can be used as sources of economically important peptides or proteins (EP 319353); or are enriched in nutritionally important amine acids so that transformed plants or their organs, in which the proteins are expressed, can be used as food with enhanced nutritional value for animals or humans (EP 318341).

Coding sequences of particular usefulness for transforming monocots to render them insect-resistant are the genes isolated from *Bacillus thuringiensis* ("Bt") strains and truncated portions thereof that code for insecticidal crystal proteins and their insecticidal polypeptide toxins (for a review, see: Höfte and Whiteley (1989) Microbiol. Rev. 53:242). The following Bt genes are believed to be particularly important for insect control in cereals (e.g., rice, wheat, corn and barley): the CryIAb gene (EP 193259) and CryIAc gene for control of *Helicoverpa* species (e.g., *H. zea* and *H. armigera*); the CryIAb gene and the CryIb gene (EP 358557) for control of *Ostrinia* species (e.g., *O. nubilalis*) in corn; the CryIAc gene for the control of *Agrotis* species in con and wheat; and the CryID and CryIE genes (EP 358557) for the control of *Spodoptera* species (e.g., *S. frugiperda*) in corn. To achieve sufficient expression of such genes in tissues of transgenic plants, it is preferred that the genes be modified as described in PCT application PCT/EP 91/00733 (PCT publication WO 91/16432).

Selectable markers in accordance with this invention can be encoded by chimaeric genes in which the coding sequences encode proteins which confer on the plant cells, in which they are expressed, resistance to a selective agent such as an antibiotic and/or herbicide. Screenable markers in accordance with this invention can be encoded by chimaeric genes in which the coding sequences encode proteins which confer on the plant cells, in which they are expressed, a different appearance, such as a different color, making plants transformed with the screenable marker separable manually. The selection of coding sequences for a selectable or screenable marker, preferably a selectable marker, for transforming a monocotyledonous plant in accordance with this invention is not believed to be critical, and it is believed that coding sequences for conventional selectable and screenable markers can be used (see, for example, the markers listed in Weising et al (1988) supra). Examples of suitable coding sequences for selectable markers are: the neo gene (Beck et al (1982) Gene 19:327) that codes for the enzyme neomycin phosphotransferase which confers resistance to the antibiotic kanamycin; the hvg gene (Gritz and Davies (1983) Gene 25:179) that codes for the enzyme hygromycin phosphotransferase which confers resistance to the antibiotic hygromycin; and the bar gene (EP 242236) that codes for phosphinothricin acetyl transferase which confers resistance to the herbicidal compounds phosphinothricin and bialaphos. In using a selectable marker gene coding for a protein that confers tolerance or resistance to a herbicide or other selective agent that acts on chloroplast metabolism, such as the bar gene, it is preferred that the marker gene be part of a chimaeric gene together with a chloroplast targeting sequence as described above. Examples of suitable coding sequences for screenable markers are the gus gene (Jefferson et al (1986) PNAS 6:3901) encoding beta-glucuronidase and the luciferase gene (Ow et al (1986) Science 234:856).

During the culturing of transformed cell aggregates of this invention, the selection pressure, provided by the presence of a selective agent in the culture media, should be high enough and should be maintained long enough to separate transformed cells from untransformed cells. It is believed, however, that particular selection pressures and durations are not critical and that the chaise of selection pressures and their durations can be made in a conventional manner. However, when the bar gene is used as a selectable marker gene, phosphinothricin (PPT) is preferably used in concentrations of about 0.5 mg to 50 mg, particularly 2 mg to 20 mg, per liter of the culture medium.

Morphogenic sectors, preferably embryogenic sectors, of morphogenic callus, preferably embryogenic callus, produced in a culture of transformed cells of electroporated walled cell aggregates (e.g., from suspension cultures) of this invention, can then be regenerated into phenotypically normal (e.g., mature and fertile) plants in a conventional manner (see, e.g., references in Vasil (1988) supra, Lazzeri and Lörz (1988) supra, and Lynch et al (1991) In "Rice Biotechnology" ed. Khush and Toenniessen, C.A.B. International, United Kingdom, p. 135 and references cited therein). The regenerated plants, thus obtained, will be transgenic and will at least contain and DNA fragments encoding a selectable or screenable marker, preferably a selectable marker, stably integrated into their nuclear genome. The presence and expression of other genes of interest can then be evaluated in a conventional manner, such as by means of Southern blotting and/or by the polymerase chain reaction (Sambrook et al (1989) Molecular Cloning: A Laboratory Manual, Second Edition, Cold Spring Harbor Laboratory Press, N.Y.) and/or by ascertaining the phenotypic expression of the genes of interest.

For the purposes of this invention, a phenotypically normal plant as produced by the transformation and regeneration procedures of this invention should be understood as at least one plant that does not differ substantially from an untransformed plant of the same line in any of its phenotypic characteristics except in those characteristics that are added or changed due to the expression of the DNA fragment(s) introduced in the plant's genome during transformation in accordance with this invention. Of course, any procedure that results in transgenic plants usually produces a number of transgenic plants that display a variety of phenotypes, only some of which are phenotypically normal as defined above.

The method of this invention can be applied to all monocotyledonous plant species, from which liquid cultures of suspended walled cells, particularly liquid cultures of walled cell aggregates, such as suspension cultures, preferably suspension cultures from which regenerable callus, particularly embryogenic callus, can be obtained by in vitro culture of explants derived from various explant sources such as immature and mature zygotic embryos, leaf bases, young inflorescences, anthers, microspores, etc. The method will be especially useful or the transformation of economically important gramineous crops, particularly the major cereals, such as rice, wheat, oats, barley, corn, sorghum, rye and millet. The resulting transgenic plants of this invention can be used to create, in a rapid and efficient manner, novel lines and/or cultivate of high agronomic value.

This invention provides a rapid, efficient and reproducible method for transforming walled cells of monocotyledonous plants by: electroporation of cultures of the suspended cells (e.g., cell suspension cultures), as well as walled cells capable of forming such cultures (e.g., cells obtained from explant-derived callus). When regenerable (e.g., embryogenic) suspension cultures of walled cells are electroporated in accordance with this invention, cultures of transformed morphogenic callus can be produced, from which phenotypically normal, fertile plants can be regenerated. This is surprising as electroporation of such walled cells, particularly those embryogenic suspension cultures, has generally not been regarded as a suitable method for obtaining stable transformants in monocotyledonous plants (see, e.g., Potrykus (1991) Annu. Rev. Plant Physiol. Plant mol. Biol. 42:205). The electroporation of such walled cells, particularly without any enzymatic or mechanical pretreatment thereof, in accordance with this invention is a distinct improvement on existing monocot transformation methods. Because the method of this invention requires only a relatively short period of in vitro culture, the method is far less time and labor consuming than most previous methods. The short tissue culture period also ensures that the occurrence of somaclonal variation is reduced.

The method of this invention can be used to produce novel, phenotypically normal (e.g., fertile), transgenic monocotyledonous plants, particularly gramineous plants, quite particularly cereals, most particularly rice, wheat and barley, which are transformed with at least one (e.g., foreign) gene of interest, stably integrated into their nuclear genome. The method is believed to be relatively independent of the genotype of the plant, being transformed, and capable of transforming cells of any plant, from which regenerable (e.g. embryogenic) suspension cultures can be obtained from at least one of its tissues. This makes it possible to transform the majority of monocot species and a substantial number of lines within each species. Indeed, the capacity to form suitable regenerable suspension cultures can be transferred, by means of classical breeding programs, from one plant line that posesses such capacity to another line that does not, making the method of this invention applicable to even more plant lines.

As described above, stably transformed monocotyledonous plant cells can be advantageously obtained by electroporation of cultures of suspended walled plant cells in accordance with this invention. In this regard, if regenerable callus (such as embryogenic callus) can be obtained from the cultures of suspended cells, some of the so-transformed plant cells of the callus can subsequently be regenerated in accordance with this invention into transgenic monocotyledonous plants that contain at least one gene of interest stably integrated into the genome of all of its cells.

However, it is believed that a culture of suspended cells of this invention need not be a "cell suspension culture" in the strict sense of the term as it is used with respect to a cell culture to be used for the preparation of protoplasts. Indeed, it is believed that, in accordance with this invention, essentially the same results in the transformation and regeneration of plant cells can be obtained by electroporation of any culture of plant cells which retain their cell wall sandals suspended in a liquid (e.g., aqueous) medium. In this regard, a culture of suspended cells of this invention should be understood as encompassing any liquid culture of cell aggregates obtained from plant tissue or from a callus obtained from plant tissue. In fact, the use of a liquid culture of suspended cell aggregates obtained from callus in the method of this invention could further reduce in vitro culture time and any subsequent somaclonal variation in transformed cells and/or plants. Furthermore, it appears that essentially the same results can be obtained by electroporation of cells from a certain type of callus for each plant species which can be used to form a culture of suspended cells of this invention. For example, in rice, such callus can be part of explant-derived (e.g., embryo-derived) embryogenic callus and consist of compact yellow and/or whitish, often round- or oval-shaped, cell clumps that can be easily separated from the rest of the callus tissue.

The Examples, which follow, illustrate this invention. Unless otherwise indicated, all experimental procedures for manipulating recombinant DNA were carried out by the standardized procedures described in Sambrook et al (1989) Molecular Cloning: A Laboratory Manual, Cold Spring Harbor Laboratory Press, N.Y. Any oligonucleotides were designed according to the general rules outlined by Kramer and Fritz (1968) Methods in Enzymology 154:350 and synthesized by the phosphoramidite method of Beaucage and Caruthers (1981) Tetrahadron Letters 22:1859 on an Applied Biosystems 380A DNA synthesizer (Applied Biosystems B. V., Maarssen, Netherlands). The compositions of the 2N6, N67, AA, N683, and hormone-free N6 media, used in the Examples, were kindly provided by Japan Tobacco Inc., Plant Breeding and Genetics Research Laboratory, 700 Higashibara, Toyoda, Iwata, Shizuoka 438, Japan.

In the following Examples, reference will be made to the following sequence listing:
Sequence Listing
SEQ ID no. 1—Sequence of plasmid pDE110 of Example 2.
SEQ ID no. 2—Sequence of plasmid pDE4 of Example 4.

EXAMPLE 1

Establishment and maintenance of rice cell suspension cultures

Cell suspension cultures of the rice cultivate *Nipponbare* and *Kochihibiki* were made from seed-derived callus as follows. Mature dry rice seeds were dehulled, surface sterilized and plated on solid 2N6 medium(N6 medium as described by Chu et al (1975) Sci.Sin.Peking 18:659 supplemented with 0.5 mg/l nicotinic acid, 0.5 mg/l pyridoxine HCl, 1.0 mg/l thiamine HCl, 2.0 mg/l 2,4 dichlorophenoxyacetic acid (2,4-D), 30 g/l sucrose, 2.0 g/l Gelrite, pH 5.8). The plates were incubated at 30° C. for 4 weeks, after which, approximately one gram of compact whitish and/or yellow parts of embryo-derived compact and embryogenic callus was transferred to 65 ml AA medium (macronutrients, amine acids, growth regulators and sugar as described for the A medium of Toriyama and Hinata (1985) Plant Science 41:179 with micronutrients and vitamins from the MS medium as described by Murashige and Skoog (1962) Physiol. Plant. 15:473, pH 5.8) in a 250 ml Erlenmeyer flask. These cultures were maintained in the dark on a rotary shaker at approximately 20 rpm. The cultures were subcultured weekly.

After the first subculture, all AA medium was removed from the culture flask and replaced by 65 ml fresh AA liquid medium. During subsequent subcultures, 1 to 2 ml of packed cell volumes of smaller, usually creamy or yellow, cell clumps, which were formed when bigger cell clusters dissociated into smaller fragments, were selected and transferred to 65 ml fresh AA medium. At each subculture, care was taken to eliminate cell clusters with brown ureas (necrosis). After 1–2 months of subculture, clean (i.e., no brown cell clusters) suspension cultures, consisting well dispersed and compact cell aggregates of different sizes, were obtained.

The cell suspension cultures of the two cultivate were then maintained by transferring 1 ml packed cell volumes to 65 ml fresh medium during each subculture. The cell clusters of the suspensions were regularly checked for their potential of regenerating plants by plating them on N683 medium (N6 medium, but with major salts at half strength, supplemented with 0.5 mg/l nicotinic acid, 0.5 mg/l pyridoxine HCl, 1.0 mg/l thiamine HCl, 876 mg/l glutamine, 266 mg/l aspartic acid, 174 mg/l arginine, 7.5 mg/l glycine, 1.0 g/l casamino acids, 0.2 mg/l naphthaleneacetic acid (NAA), 1.0 mg/l kinetin, 20 g/l sucrose, 4.0 g/l Gelrite, pH 5.8) for plant regeneration.

EXAMPLE 2

Transformation of rice cell suspension cultures with a herbicide resistance gene The cell suspension cultures from rice cultivate *Nipponbare* and *Kochihibiki* of Example 1 were transformed with a herbicide resistance gene, and transformed cells were regenerated into transgenic plants as follows.

1. Nipponbare

A cell suspension culture was established and maintained for a period of two months. Four days after the last subculture, the AA culture medium was removed, the cell clusters were washed with electroporation buffer AA (35 mM L-aspartic acid, 35 mM L-glutamic acid, 5 mM D-gluconic acid, 5 mM 2-[N-morpholino] ethane sulfonic acid (MES), 0.4M mannitol, pH 5,8 (Tada et al (1990) Theor. Appl. Genet. 80:475)) and kept in this buffer for one hour on a shaker at 30 rpm. Thereafter, the cell aggregates were washed twice with electroporation buffer AA. Approx. 75 mg to 100 mg of cell clusters were transferred to electroporation cuvettes and resuspended in approx. 100 to 150 µl electroporation buffer AA. 15 µg of pDE110 plasmid DNA, linearized with HindIII, were added to each cuvette. Plasmid pDE110 is a plasmid with a length of 4883 bp and contains the phosphinothricin (PPT) resistance gene (bar) under control of the CaMV 3583 promoter (EP 359617). The complete sequence of pDE110 is given in SEQ ID no. 1. After addition of the plasmid DNA, the cuvettes were put on ice for 10 min. Then, a single pulse with a field strength of 700 V/cm was discharged from a 800 82 F capacitor to the mixture of cell clusters and DNA. Immediately after the pulse, liquid N67 medium (N6 medium supplemented with 0.5 mg/l nicotinic acid, 0.5 mg/l pyridoxine HCl, 1.0 mg/l thiamine HCl, 1.0 mg/l 2,4 D, 0.5 mg/l 6-benzyleminopurine, 20 g/l sucrose, 30 g/l sorbitol, pH 5.8) was added to the cell clusters, which were then plated on to solid selective N67 medium (N6 medium supplemented with 0.5 mg/l nicotinic acid, 0.5 mg/l pyridoxine HCl, 1.0 mg/l thiamine HCl, 1.0 mg/l 2,4-D, 0.5 mg/l 6-benzylaminopurine, 20 g/l sucrose, 30 g/l sorbitol, 2.0 g/l Gelrite, pH 5.8) containing 5 mg/l PPT.

The plates were incubated at 26° C. under a light/dark regime of 16/8 hours. After 6 weeks of culture, PPT-resistant calli developing from the treated suspension aggregates were placed on fresh N67 medium plus PPT for another 12 days. Thereafter, PPT-resistant calli were transferred to plant regeneration medium N623 supplemented with 5 mg/l PPT. From two of the selected calli, plants could be regenerated. As soon as the developing plantlets reached a height of approximately 10 cm (usually within one to two months), they were transferred to hormone-free N6 medium (N6 medium supplemented with 0.5 mg/l nicotinic acid, 0.5 mg/l pyridoxine HCl, 1.0 mg/l thiamine HCl, 1.0 g/l casamino acids (vitamin assay), 20 g/l sucrose, 2.0 g/l Gelrite, pH 5.8) end cultured on this medium until they were strong enough to be transferred to soil and to the greenhouse (usually after a period of one to three weeks).

2. Kochihibiki

A cell suspension culture was established and maintained for a period of 4.5 months. Four days after the last subculture, the AA culture medium was removed, the cell clusters were washed with electroporation buffer 9 (0.4M mannitol, 10 mM KCl, 4 mM $CaCl_2.2H_2O$, 10 mM N-2-hydroxyethylpiperazine-N'-2-ethanesulfonic acid (HEPES), pH 7.2) and kept in this buffer on a shaker for one hour. Thereafter, the cell clusters were washed twice with electroporation buffer 9. Approx. 75 to 100 mg of cell aggregates were transferred to electroporation cuvettes end resuspended in approximately 100 to 150 µl electroporation buffer 9 per cuvette. 12 µg of pDE110 plasmid DNA, linearized with EcoRI, were added to each cuvette and coincubated with the cell clusters for 45 min at room temperature (25° C.). The cuvettes were placed on ice for 10 min., and the cell aggregates in each cuvette were electroporated by applying a single pulse discharged from a capacitor with one of the following voltage-capacitance characteristics: 700 V/cm-800 µF (4 cuvettes), 600 V/cm-900 µF (4 cuvettes), 700 V/cm-900 µF (5 cuvettes). Liquid N67 medium was added to each cuvette immediately after the pulse, and the cell clusters were plated on solid selective N67 medium supplemented with 5 mg/l PPT.

The plates were incensed at 26° C. under a light/dark regime of 16/8 hours for 19 days. Developing PPT-resistant calli were isolated and transferred to fresh N67 medium plus 5 mg/l PPT and propagated for another 18 days. After this second selection cycle, the well-developing PPT-resistant calli were place on plant regeneration medium N683 supplemented with 5 mg/l PPT. Plants were regenerated from 17 of the selected calli; five calli were from cell aggregates electroporated with a 700 V/cm-800 µF pulse; two calli were from cell aggregates electroporated with a 600 V/cm-900 µF pulse; and ten calli were from cell aggregates electroporated with a 700 V/cm-900 µF pulse. As soon as the developing plantlets reached a height of approximately 10 cm (usually within one to two months), they were transferred to hormone-free N6 medium and cultured on this medium until they were strong enough to be transferred to soil and to the greenhouse (usually after a period of one to three weeks).

In a second round of experiments, the same *Kochihibiki* suspension culture, described above, was used 5 months after initiation. Five days after the last subculture, the cell clusters were washed in electroporation buffer 9, kept for 45 min. in this buffer on a shaker, and washed twice thereafter with the same buffer. Approximately 75 to 100 mg of cell clusters were transferred to each of 16 electroporation cuvettes and resuspended in approximately 100 to 150 µl electroporation buffer 9 per cuvette. 15 µg of pDE110 plasmid DNA, linearized with HindIII, were added to each cuvette. Eight of these cuvettes (batch A) were put on ice for 10min and then pulsed; the other eight cuvettes (batch B) were kept at room temperature for one hour prior to electroporation. Pulses of 600 V/cm-900 µF (four cuvettes from each batch) and 700 V/cm-900 µF (four cuvettes from each batch) were applied to the mixture of cell clusters and DNA. Immediately after the pulse, N67 liquid medium was added to each cuvette, and the cell clusters were plated on selective N67 medium supplemented with 5 mg/l PPT.

The plates were incubated as above. After 23 days, the developing PPT-resistant calli derived from plated suspension clusters were transferred to fresh selective N67 medium plus 5 mg/l PPT for a second selection cycle and further propagation. After 21 days, well growing calli were transferred to plant regeneration medium N683 plus 5 mg/l PPT. Plants could be regenerated from 24 of the selected calli; two calli were from cell aggregates of batch A electroporated with a 600 V/cm-900 µF pulse; three calli were from cell aggregates of batch A electroporated with a 700 V/cm and 900 µF pulse; nine calli were from cell aggregates of batch B electroporated with a 600 V/cm-900 µF pulse; and ten calli were from cell aggregates of batch B electroporated with a 700 V/cm-900 µF pulse. As soon as the developing plantlets reached a height of approximately 10 cm (usually within one to two months), they were transferred to hormone-free N6 medium and cultured on this medium until they were strong enough to be transferred to soil and to the greenhouse (usually after a period of one to three weeks).

EXAMPLE 3

Analysis of the transgenic plants from Example 2

The plants of Example 2 were cultivated in the greenhouse and sprayed with a 0.5% Basta (PPT) solution 4–6 weeks after transfer to soil. All of the plants were Basta-resistant, whereas non-transformed control plants turned brown and died within one week after herbicide treatment.

Southern analysis was performed on 13 selected primary transformants (in vitro plants derived from 13 separate regenerating calli). For Southern analysis, the rice was digested with the restriction enzymes, EcoRV, BglII and PvuII, Southern blotted, and probed with pDE110 DNA. The Southern analysis showed that three of the plants carried single copy inserts of the complete pDE110-derived chimaeric bar gene (i.e., the bar gene with promoter and 3' untranslated end), integrated into the rice genome. Five of the plants had one to three copies of pDE110-derived DNA integrated into their genome, with at least one of the copes containing the complete chimaeric bar gene. Three of the plants carried multiple inserts of pDE110-derived DNA, while two other plants had only parts of the chimaeric bar gene integrated into the genome.

Three of the plants, regenerated from one of two independently transformed calli of Nipponbare of Example 2.1, were grown to maturity and set seed. One of these plants was analyzed in detail. Southern analysis of this plant proved that its genome contained an insert, at a single locus in the rice genome, that comprises one almost complete copy of the transforming DNA (pDE110), including the P35S-bar-3'nos chimeric gene. From this plant (designated as E253), S1 seeds (after selfing) were harvested. Some of the seeds were used for an analysis of the segregation of the bar gene in the progeny plants. 93 seedlings were sprayed with Basta: 73/93 seedlings were Basta resistant, 20/93 seedlings were Basta sensitive ($X^2=0.52$, which is not significantly different from Mendelian segregation at a single dominant locus). Four of the Basta-resistant progeny plants were analyzed in Southern blots. All four plants had the same hybridization pattern as determined for primary transformant E253.

For Kochihibiki, integration of the transforming DNA was confirmed by Southern analysis of in vitro shoots or regenerated plants obtained from various calli. One regenerated plant (designated as X32), obtained from one of the 24 independently transformed calli of Example 2.2 was analyzed in more detail and was shown to contain an almost complete copy of the transforming DNA (pDE110), including the complete P35S-bar-3'nos chimeric gene. From primary transformant K32, the S1 seeds were harvested, and segregation of the bar gene was analyzed in 98 progeny plants by Basta spraying: 80/98 seedlings were Basta-resistant, 18/98 seedlings were Basta-sensitive ($X^2=2.36$, which is not significantly different from Mendelian segregation at a single dominant locus). Four of the Basta-resistant progeny plants were analyzed in Southern blots. All four plants had the same hybridization pattern as determined for primary transformant K32.

EXAMPLE 4

Transformation of seed-derived callus cells

Mature dry seeds of the rice cultivars *Kochihibiki* and *Chiyonishiki* were dehulled, surface sterilized and plated on solid 2N6 medium. The plates were incubated at 30° C. for approximately 1 month. Embryogenic suspension cultures were then initiated using the small, round- and oval-shaped, yellow and whitish callus clumps (some of which have globular structures on the surface which may represent proembryos) that appeared in the resulting callus and that constituted the majority of the observed callus types in the culture or were located at the surface of larger calli. These callus clumps were usually not attached to the surfaces of the larger calli or to each other, and they were easily removed individually with a pair of forceps.

The callus clumps, with an average maximum diameter of about 2 mm, were carefully transferred immediately to electroporation buffer 9 and kept in this buffer for one hour on a shaker (30 rpm). Thereafter, the callus clumps were washed once with electroporation buffer 9. Approx. 75 to 100 mg of callus clumps were transferred to electroporation matts, and resuspended in approx. 150 µl buffer 9. 10 µg of pDE4 plasmid DNA were added to each cuvette. Plasmid pDE4 is a plasmid with a length of 5642 bp and contains a gene (gus) encoding beta-glucuronidase (Jefferson et al (1986) PNAS 83:8447) under the control of the CaMV 35S3 promoter (EP 359617). The complete sequence of pDE4 is given in SEQ ID no. 2. The plasmid DNA was coincubated with the callus clumps for 45 min. at room temperature. The cuvettes were then placed on ice for 10 min. Thereafter, a single pulse with a field strength of 600 V/cm was discharged from a 900 µF capacitor to the mixture of callus clumps and DNA. Immediately after the pulse, liquid AA medium was added to each cuvette, and the callus clumps were transferred to a petri dish (3.5 mm diameter). The liquid was removed and replaced by 2 ml AA medium per petri dish. The callus clumps were cultured in the dark for 5 days. Thereafter, the callus clumps were transferred to X-gluc (5-bromo-4-chloro-3-indolyl glucuronide) solution for in situ detection of beta-glucuronidase (GUS) activity (as described in Denecke et al (1989) Methods in Mol. and Cell. Biol., Jan/Feb 1989, 19–27). After incubation for 24 to 48 hours at 37° C. the blue-colored products of GUS activity were visible, and the number of blue areas (i.e., blue cells indicating GUS expression) was counted under a stereo microscope. Approx. 30% of the treated callus clumps showed one or several blue areas (*Kochihibiki:* 12 of 41 electroporated callus clumps; *Chiyonishiki:* 10 of 35 electroporated callus clumps).

EXAMPLE 5

Establishment and maintenance of rice cultures of suspended cell clumps

Immature zygotic embryos were isolated from surface sterilized developing rice kernels (in milky stage) of greenhouse-grown plants of the rice cultivars *Kochihibiki* and *Chiyonishiki*. The immature embryos were placed, embryo axis towards the medium, on solid 2N6 medium (see Example 1). The plated explants were kept at 27° C. in darkness. Within 2–3 weeks after culture initiation, small compact yellowish callus clumps with a smooth surface grew out from primary callus and directly from the explant. Approximately 30 of such callus clumps of different size, with diameters of between 0.1 mm and 2.0 mm, were each transferred into 65 ml of N6 liquid medium (Chu et al (1975) supra), supplemented with 0.3 g/l casamino acid (vitamin assay), 30 g/l sucrose and 1 mg/l 2,4-D, in a 250 ml Erlenmeyer flask. These flasks with the cultures were kept in the dark on a rotary shaker at approximately 120 rpm. Subculturing was done weekly; at the first subculture (one week after culture initiation), soft and whitish callus pieces were discarded, and all medium was removed and replaced by 65 ml of fresh N6 liquid medium. The same procedure was used at the second subculture (2 weeks after culture initiation). During the first two weeks, the original callus clumps grew into bigger pieces. An the third week of culture, newly developed small cell aggregates started to separate from the bigger callus clumps. At the third subculture, these smaller aggregates and the big yellow compact pieces were selected and transferred to fresh liquid N6 medium At the fourth subculture, only small compact yellow clumps were selected and transferred to fresh medium; the bigger clumps were discarded. At the following subcultures, 1-2 ml packed cell volume (PVC) of selected small compact yellow aggregates were tranferred to 65 ml fresh N6 medium.

EXAMPLE 6

Tranformation of rice cultures of suspended cell clumps

The cultures of suspended cell clumps from rice cultivars *Kochihibiki* and *Chiyonishiki* of Example 5 were transformed with a herbicide resistance gene, and transformed cells were regenerated into transgenic plants as follow:

1. *Kochihibiki*

A culture of suspended cell clumps was established and maintained in N6 medium for 18 days prior to electroporation. Four days after the second weekly subculture, the N6 medium was removed, the cell clumps were washed with electroporation buffer 9 and then kept in this buffer for 1 hour at room temperature. The cell clumps were washed in buffer 9 again and transferred to electroporation cuvettes and resuspended in approximately 120 μl of buffer 9. About 13 μg of pDE110 DNA, linearized with HindIII, was added per cuvette, and the mixture of cell aggregates in buffer 9 and DNA was incubated, first for 45 min at room temperature and then for 10 min on ice. Then, a single pulse with a field strength of 650 V/cm was discharged from a 900 μF capacitor to the mixture of cell clumps and DNA. Liquid N67 medium was then added to the cuvettes, and the electroporated cell clumps were transferred to solid N67 medium supplemented with 5 mg/l PPT. After 23 days, the developing calli were transferred to fresh N67 medium plus PPT. After another 21 days on selective N67 medium, the selected calli were transferred to selective regeneration medium. After 35 days on regeneration medium, shoots were transferred to N6 hormone-free medium. For each callus, three in vitro plantlets of approximately 10cm height were transferred to soil and to the greehouse.

In similar experiments, cultures of suspended cell aggregates were electroporated 6 days or 12 days after establishing the culture. From these experiments, transformed calli were obtained, from which transgenic plants were regenerated.

2. *Chiyonishiki*

A culture of suspended cell clumps was established and maintained using essentially the sue procedures as described above for *Kochihibiki* in Example 6.1. However, cell clumps for electroporation were harvested four days after the third weekly subculture. Electroporation, subsequent callus initiation and propagation, and regeneration of plants were also carried out essentially as described in Example 6.1. Some of the cell clumps were electroporated with pDE110, and other cell clumps were electroporated with plasmid DNA hat contained both a chimeric bar gene and another chimaeric gene containing the DNA coding for barstar under the control of one of the following stamen-specific promoters of rice: PT72, PT42 and PE1 (WO 92/00274).

EXAMPLE 7

Analysis of transgenic plants of Example 6

Six *Kochihibiki* plants of Example 6.1, derived from two independent transgenic callus lines, were cultivated in the greenhouse, were sprayed with Basta, and were found to be Basta-resistant.

Two plants, designated as KB25 and KB28, each of which was derived from a different transgenic callus line, were analyzed in detail. Both plants scored positive in enzymatic assays for phosphinotricin acetyl transferase (PAT) activity. For Southern analysis, the rice genomicDNA was digested with the restriction enzymes XhoI, BglII and PvuII, Southern blotted and probed with pDE110 DNA. In both plants, the pDE110-derived DNA was found to be located on a single XhoI restriction fragment. KB25 and KB28 both contained a functional 35S promoter linked to the complete bar gene as indicated by the 1.54 kb BglII fragment and the 1.65 kb PvuII fragment. KB25 carried multiple inserts, and KB28 carried 1 to 4 copies of pDE110-derived DNA. Both plants were found to set seed.

Plants regenerated from a selected callus of Example 6.2, after transformation with pDE110, were cultivated in the greenhouse, sprayed with Basta, and were found to be Basta-resistant. One plant, designated as CB23, scored positive in a PAT assay and was found to contain 1–3 almost complete copies of pDE110 DNA in a Southern hybridization performed as described above for *Kochihibiki*.

Plants regenerated from selected calli of Example 6.2, after transformation with DNA containing two chimaeric genes, including the barstar gene, were found to be Basta-resistant, to be PAT-positive, and to contain both the chimaeric bar gene and the chimaeric barstar gene. Expression of the barstar gene in immature spikelets is determined by Northern analysis.

---

We claim:

1. A process for integration of a DNA fragment in the genome of a cell of a rice plant, comprising the steps of: providing without any enzymatic pretreatment or mechanical cell wall removal thereto, a culture of aggregated suspended intact plant cells; preplasmolyzing said culture of aggregated suspension plant cells by suspension in a hypertonic buffer;

transforming cells from said culture with a DNA fragment by electroporation of said cells in the presence of said DNA fragment; optionally regenerating, from said transformed cell, a transformed phenotypically normal plant.

2. The process of claim 1, wherein said culture of suspended plant cells, is a culture of suspended cell clumps.

3. The process of claim 1, wherein said culture of suspended plant cells, is a cell suspension culture.

4. The process of claim 3, wherein said culture of suspended plant cells, is a regenerable cell suspension culture.

5. The process of claim 3, wherein said culture of suspended plant cells, is an embryogenic cell suspension culture.

6. The process of claim 2, wherein said culture of suspended cells is not older than about four months.

7. The process of claim 2, wherein said culture of suspended cells is not older than about three months.

8. The process of claim 2, wherein said culture of suspended cells is transformed not later than about 25 days after initiation of said culture of suspended cells.

9. The process of claim 2, wherein said culture of suspended cells is transformed not later than about 18 days after initiation of said culture of suspended cells.

10. The process of claim 2, wherein said culture of suspended cells is transformed not later than about 12 days after initiation of said culture of suspended cells.

11. The process of claim 2, wherein said culture of suspended cells is transformed not later than about 6 days after initiation of said culture of suspended cells.

12. The process of claim 2, wherein said culture of suspended cells is transformed immediately after initiation of said culture of suspended cells.

13. The process of claim 3, wherein 75% of the cells of said culture of suspended cell clumps have a normal chromosome number.

14. The process of claim 3, wherein 80% of the cells of said culture of suspended cell clumps have a normal chromosome number.

15. The process of claim 3, wherein 90% of the cells of said culture of suspended cell clumps have a normal chromosome number.

16. The process of any one of claims 1 to 15, wherein said preplasmolysis is achieved by suspension in a hypertonic buffer for a period of about 15 minutes to about 3 hours.

17. The process of claim 16, wherein said preplasmolysis is achieved by suspension in a hypertonic buffer for a period of about 45 minutes to about 1.5 hours.

18. The process of anyone of claim 1–15, wherein said hypertonic buffer comprises mannitol at a concentration of at least 0.4M.

19. The process of claim 1, wherein said electroporation is carried out in a cuvette containing: 30 to 150 mg of cell aggregates of said culture of suspended cells; and 5 to 30 μg of said DNA fragment.

20. The process of claim 19, wherein said cuvette contains 75 to 100 mg of cell aggregates of said culture of suspended cells.

21. The process of claim 19, wherein said cuvette contains 10 to 20 μg of said DNA fragment.

22. The process of claim 19, wherein the electroporation is carried out by discharging a single pulse with an initial field strength of between 600 to 700 V/cm from a capacitor with a capacitance of between 800 to 900 μF.

23. The process of claim 19, wherein said cuvette contains 100 to 200 μl of electroporation buffer.

24. The process of anyone of claims 1–15, wherein said culture of suspended plant cells is derived from rice cultivars *Chiyonishiki, Nipponbare* or *Kochihibiki*.

25. The process of claim 16, wherein said culture of suspended plant cells is derived from rice cultivars *Chiyonishiki, Nipponbare* or *Kochihibiki*.

26. The process of claim 22, wherein said culture of suspended plant cells is derived from rice cultivars *Chiyonishiki, Nipponbare* or *Kochihibiki*.

* * * * *

UNITED STATES PATENT AND TRADEMARK OFFICE
CERTIFICATE OF CORRECTION

PATENT NO. : 5,679,558
DATED : October 21, 1997
INVENTOR(S) : Gobel et al.

Page 1 of 12

It is certified that error appears in the above-indentified patent and that said Letters Patent is hereby corrected as shown below:

Column 1, line 36, after "has" please delete "boon" and substitute --been-- therefor.

Column 1, line 55, before "encoding" (both occurrences) please delete "gone" and substitute --gene-- (both occurrences) therefor.

Column 2, line 20, after "(e.g., fertile)" and before "can" please delete "pints" and substitute --plants-- therefor.

Column 2, line 55, after "mainly" and before "means" please insert --by--.

Column 2, line 57, after "case," and before "callus" please insert --embryogenic)--.

UNITED STATES PATENT AND TRADEMARK OFFICE
CERTIFICATE OF CORRECTION

PATENT NO. : 5,679,558
DATED : October 21, 1997
INVENTOR(S) : Gobel et al.

It is certified that error appears in the above-indentified patent and that said Letters Patent is hereby corrected as shown below:

Column 2, line 61, after "cultures" and before "cereals" please insert --of--.

Column 6, line 40, after "agent" and before "depend" please delete "wall" and substitute --will-- therefor.

Column 7, line 19, before "expression" please delete "or" and substitute --for-- therefor.

Column 7, line 38, before "(Franck et al" please delete "CabbB-B" and substitute --CabbB-S-- therefor.

Column 7, line 41, after "the" and before "promoter" please delete "3583" and substitute -35S -- therefor.

UNITED STATES PATENT AND TRADEMARK OFFICE
CERTIFICATE OF CORRECTION

PATENT NO. : 5,679,558
DATED : October 21, 1997
INVENTOR(S) : Gobel et al.

It is certified that error appears in the above-indentified patent and that said Letters Patent is hereby corrected as shown below:

Column 8, line 2, before "of" please delete "monsters" and substitute --monocots-- therefor.

Column 8, line 2, after "Such" please delete "340" and substitute --3'-- therefor.

Column 8, line 5, after "chimaeric" and before "containing" please delete "gone" and substitute --gene-- therefor.

Column 8, line 9, before "and" please delete "Veltan" and substitute --Velten-- therefor.

Column 8, line 33, after "lumen" and before "the" please insert --of--.

UNITED STATES PATENT AND TRADEMARK OFFICE
CERTIFICATE OF CORRECTION

PATENT NO.   : 5,679,558
DATED        : October 21, 1997
INVENTOR(S)  : Gobel et al.

It is certified that error appears in the above-indentified patent and that said Letters Patent is hereby corrected as shown below:

Column 8, line 55, after "production" please add --of--.

Column 8, line 56, after "plants" and before "well" please delete "arm" and substitute --are-- therefor.

Column 9, line 26, after "in" and before "and" please delete "con" and substitute --corn-- therefor.

Column 10, line 24, after "contain" and before "DNA" please delete "and" and substitute --any-- therefor.

Column 10, line 56, after "useful" and before "the" please delete "or" and substitute --for-- therefor.

UNITED STATES PATENT AND TRADEMARK OFFICE
CERTIFICATE OF CORRECTION

PATENT NO. : 5,679,558
DATED : October 21, 1997
INVENTOR(S) : Gobel et al.

It is certified that error appears in the above-indentified patent and that said Letters Patent is hereby corrected as shown below:

Column 11, line 6, after "those" and before "embryogenic" please insert --of--.

Column 11, line 54, after "wall" please delete "sandals" and substitute --and are-- therefor.

Column 12, line 32, after "rice" please delete "cultivate" and substitute --cultivars-- therefor.

Column 12, line 43, after "macronutrients" please delete "amine" and substitute --amino-- therefor.

Column 12, line 44, after "the" please delete "A" and substitute --AA-- therefor.

UNITED STATES PATENT AND TRADEMARK OFFICE
CERTIFICATE OF CORRECTION

PATENT NO.   : 5,679,558
DATED        : October 21, 1997
INVENTOR(S)  : Gobel et al.

It is certified that error appears in the above-indentified patent and that said Letters Patent is hereby corrected as shown below:

Column 12, line 50, after "approximately" and before "rpm" please delete "20" and substitute --120-- therefor.

Column 12, line 59, after "brown" please delete "ureas" and substitute --areas-- therefor.

Column 12, line 61, after "consisting" and before "well" please insert --of--.

Column 12, line 64, after "two" and before "were" please delete "cultivate" and substitute --cultivars-- therefor.

Column 13, line 1, after "on" please delete "N683" and substitute --N6S3-- therefor.

UNITED STATES PATENT AND TRADEMARK OFFICE
CERTIFICATE OF CORRECTION

PATENT NO.   : 5,679,558
DATED        : October 21, 1997
INVENTOR(S)  : Gobel et al.

It is certified that error appears in the above-indentified patent and that said Letters Patent is hereby corrected as shown below:

Column 13, line 15, after "rice" please delete "cultivate" and substitute --cultivars-- therefor.

Column 13, line 36, after "CaMV" and before "promoter" please delete "3583" and substitute --35S3-- therefor.

Column 13, line 40, after "800" and before "capacitor" please delete "82F" and substitute --$\mu$F-- therefor.

Column 13, line 45, before "20" please rewrite "6-benzyleminopurine" as --6-benzylaminopurine--.

UNITED STATES PATENT AND TRADEMARK OFFICE
CERTIFICATE OF CORRECTION

PATENT NO. : 5,679,558
DATED : October 21, 1997
INVENTOR(S) : Gobel et al.

It is certified that error appears in the above-indentified patent and that said Letters Patent is hereby corrected as shown below:

Column 13, line 57, after "medium" and before "supplemented" please delete "N623" and substitute --N6S3-- therefor.

Column 13, line 65, before "cultured" please delete "end" and substitute --and-- therefor.

Column 14, line 11, after "cuvettes" and before "resuspended" please delete "end" and substitute --and-- therefor.

Column 14, line 25, after "were" and before "at" please delete "incensed" and substitute --incubated-- therefor.

UNITED STATES PATENT AND TRADEMARK OFFICE
CERTIFICATE OF CORRECTION

PATENT NO. : 5,679,558
DATED : October 21, 1997
INVENTOR(S) : Gobel et al.

It is certified that error appears in the above-indentified patent and that said Letters Patent is hereby corrected as shown below:

Column 14, line 30, after "were" and before "on" please delete "place" and substitute --placed-- therefor.

Column 14, line 30, after "medium" and before "supple" please delete "N683" and substitute --N6S3-- therefor.

Column 14, line 66, after "medium" and before "plus" please delete "N683" and substitute --N6S3-- therefor.

Column 15, line 25, after "rice" and before "was" please insert --DNA--.

Column 15, line 33, after "the" please delete "copes" and substitute --copies-- therefor.

UNITED STATES PATENT AND TRADEMARK OFFICE
CERTIFICATE OF CORRECTION

PATENT NO. : 5,679,558
DATED : October 21, 1997
INVENTOR(S) : Gobel et al.

It is certified that error appears in the above-indentified patent and that said Letters Patent is hereby corrected as shown below:

Column 15, line 44, after "the" please delete "P358" and substitute --P35S-- therefor.

Column 15, line 58, after "as" and before ")" (bracket) please delete "X32" and substitute --K32-- therefor.

Column 15, line 62, after "complete" please delete "P358" and substitute --P35S-- therefor.

Column 16, line 29, before "and" please delete "matts" and substitute --curvettes-- therefor.

Column 16, line 33, after "CaMV" please delete "3583" and substitute --35S3-- therefor.

UNITED STATES PATENT AND TRADEMARK OFFICE
CERTIFICATE OF CORRECTION

PATENT NO. : 5,679,558
DATED : October 21, 1997
INVENTOR(S) : Gobel et al.

It is certified that error appears in the above-identified patent and that said Letters Patent is hereby corrected as shown below:

Column 17, line 17, before "the" please delete "An" and substitute --In-- therefor.

Column 17, line 36, after "as" please delete "follow" and substitute --follows-- therefor.

Column 18, line 2, after "the" and before "." (period) please delete "greehouse" and substitute --greenhouse-- therefor.

UNITED STATES PATENT AND TRADEMARK OFFICE
CERTIFICATE OF CORRECTION

PATENT NO. : 5,679,558
DATED : October 21, 1997
INVENTOR(S) : Gobel et al.

It is certified that error appears in the above-identified patent and that said Letters Patent is hereby corrected as shown below:

Column 18, line 10, after "the" and before "procedures" please delete "sue" and substitute --same-- therefor.

Column 18, line 17, after "DNA" please delete "hat" and substitute --that-- therefor.

Signed and Sealed this

Twenty-sixth Day of May, 1998

Attest:

BRUCE LEHMAN

*Attesting Officer*  *Commissioner of Patents and Trademarks*